(12) United States Patent
Bileschi et al.

(10) Patent No.: US 12,353,999 B2
(45) Date of Patent: Jul. 8, 2025

(54) PREDICTING BIOLOGICAL FUNCTIONS OF PROTEINS USING DILATED CONVOLUTIONAL NEURAL NETWORKS

(71) Applicant: Google LLC, Mountain View, CA (US)

(72) Inventors: Maxwell Bileschi, Waltham, MA (US); Lucy Colwell, Cambridge, MA (US); Theodore Sanderson, London (GB); David Benjamin Belanger, Cambridge, MA (US); Jamie Alexander Smith, Boston, MA (US); Drew Bryant, Snoqualmie, WA (US); Mark Andrew DePristo, Los Altos, CA (US); Brandon Carter, Cambridge, MA (US)

(73) Assignee: Google LLC, Mountain View, CA (US)

( * ) Notice: Subject to any disclaimer, the term of this patent is extended or adjusted under 35 U.S.C. 154(b) by 940 days.

(21) Appl. No.: 17/601,105

(22) PCT Filed: Apr. 10, 2020

(86) PCT No.: PCT/US2020/027616
§ 371 (c)(1),
(2) Date: Oct. 4, 2021

(87) PCT Pub. No.: WO2020/210591
PCT Pub. Date: Oct. 15, 2020

(65) Prior Publication Data
US 2022/0172055 A1      Jun. 2, 2022

Related U.S. Application Data

(60) Provisional application No. 62/832,691, filed on Apr. 11, 2019.

(51) Int. Cl.
*G06N 3/08*      (2023.01)
*G16B 20/00*    (2019.01)
(Continued)

(52) U.S. Cl.
CPC .............. *G06N 3/08* (2013.01); *G16B 20/00* (2019.02); *G16B 40/00* (2019.02); *G16B 50/10* (2019.02)

(58) Field of Classification Search
CPC .......... G06N 3/08; G16B 40/00; G16B 50/10; G16B 20/00
See application file for complete search history.

(56) References Cited

U.S. PATENT DOCUMENTS

| | | | |
|---|---|---|---|
| 6,723,698 B2 * | 4/2004 | Rueger | C07K 14/495 514/17.7 |
| 2002/0168682 A1 * | 11/2002 | Goodlett | G01N 33/6848 435/7.1 |

(Continued)

OTHER PUBLICATIONS

Akidau et al., "The dataflow model: a practical approach to balancing correctness, latency, and cost in massive-scale, unbounded, out-of-order data processing," Proceedings of the VLDB Endowment, Aug. 2015, 8(12):1792-1803.

(Continued)

*Primary Examiner* — David E Choi
(74) *Attorney, Agent, or Firm* — Fish & Richardson P.C.

(57) ABSTRACT

Methods, systems, and apparatus, including computer programs encoded on a computer storage medium, for predicting biological functions of proteins. In one aspect, a method comprises: obtaining data defining a sequence of amino acids in a protein; processing the data defining the sequence of amino acids in the protein using a neural network, wherein: the neural network is a convolutional neural network comprising one or more dilated convolutional layers; and the neural network is configured to process the data defining the sequence of amino acids in the protein in accordance with trained parameter values of the neural network to generate a neural network output characterizing at least one predicted biological function of the sequence of (Continued)

amino acids in the protein; and identifying the predicted biological function of the sequence of amino acids in the protein using the neural network output.

20 Claims, 12 Drawing Sheets

(51) Int. Cl.
   *G16B 40/00* (2019.01)
   *G16B 50/10* (2019.01)

(56) References Cited

U.S. PATENT DOCUMENTS

| | | | |
|---|---|---|---|
| 2004/0109856 A1* | 6/2004 | Mennerich | C07K 16/22 424/143.1 |
| 2008/0014646 A1* | 1/2008 | Kuroda | G16B 40/20 530/300 |
| 2016/0122451 A1* | 5/2016 | Chilkoti | A61K 47/58 525/54.1 |
| 2017/0088817 A1* | 3/2017 | Baileykobayashi | C12N 5/0623 |
| 2020/0363414 A1* | 11/2020 | Yelensky | G06N 3/045 |
| 2022/0172055 A1* | 6/2022 | Bileschi | G16B 20/00 |
| 2022/0270711 A1* | 8/2022 | Feala | G16B 45/00 |
| 2022/0336055 A1* | 10/2022 | Hamp | G06N 3/04 |
| 2023/0402133 A1* | 12/2023 | Jumper | G16B 15/30 |
| 2024/0087674 A1* | 3/2024 | Gligorijevic | G16B 15/00 |

OTHER PUBLICATIONS

Altschul et al., "Basic local alignment search tool," J. Mol. Biol., Oct. 1990, 215(3):403-410.
Andreeva et al., "SCOP database in 2004: refinements integrate structure and sequence family data," Nucleic acids research, Jan. 2004, 32:D226-D229.
Angermueller et al, "Deep learning for computational biology," Molecular system biology, Jul. 29, 2016, 12(878):1-16.
Ashkenazy et al, "ConSurf 2016: an improved methodology to estimate and visualize evolutionary conservation in macromolecule," Nucleic acids research, May 10, 2016, 44:W344-W350.
Attwood et al., "PRINTS and its automatic supplement, prePRINTS," Nucleic acids res, Jan. 2003, 31(1):400-402.
Bach et al, "On pixel-wise explanations for non-linear classifier decisions by layer-wise relevance propagation," PLoS, Jul. 10, 2015, 46 pages.
Baehrens et al, "How to explain individual classification decisions," Journal of Machine Learning Research, Jun. 2010, pp. 1803-1831.
Bairoch et al., "PROSITE: recent developments," Nucleic acids, Sep. 1994, 22(17):3583-3589.
Bateman et al., "The PFAM protein families database in 2019," Nucleic acids research, 2019, 47(D1):D427-D432.
Berezin et al., "ConSeq: the identification of functionally and structurally important residues in protein sequences," Bioinformatics, May 22, 2004, 20(8):1322-1324.
Bitbol et al, "Inferring interaction partners from protein sequences," Proceedings of the National Academy of Sciences, Oct. 25, 2016, 113(43):12180-12185.
Buljan et al, "The evolution of protein domain families," Biochemical Society Transactions, Jul. 22, 2009, 37:751-755.
Burley et al, "Protein Data Bank (PDB): the single global macromolecular structure archive," Protein Crystallography, 2017, 1607:627-641.
Carter et al., "What made you do this? Understanding black-box decisions with sufficient input subsets," arXiv, Feb. 8, 2019, 35 pages.
Caruana et al, "Intelligible models for healthcare: predicting pneumonia risk and hospital 30-day readmission," Proceedings of the 21th ACM SIGKDD International Conference on Knowledge Discovery and Data Mining, Aug. 10, 2015, pp. 1721-1730.
Chang et al, "COMBREX-DB: an experiment centered database of protein function: Knowledge, predictions and knowledge gaps," Nucleic acids research, Dec. 3, 2015, 44:D330-D335.
Cheng et al., "ECOD: an evolutionary classification of protein domains," PLoS computational biology, Dec. 4, 2014, 10(12):e1003926, 18 pages.
Chorowski et al., "End-to-end continuous speech recognition using attention-based recurrent nn: first results," arXiv, Dec. 4, 2014.
Dalkiran et al, "ECPred: a tool for the prediction of the enzymatic functions of protein sequences based on the EC nomenclature," BMC bioinformatics, Sep. 21, 2018, 19:334, 13 pages.
Dawson et al., "CATH: an expanded resource to predict protein function through structure and sequence," Nucleic acids research, 2017, 45:D289-D295.
Dean et al., "MapReduce: simplified data processing on large clusters," Communications of the ACM, Jan. 2008, 51(1):107-113.
Deng et al, "ImageNet: A large-scale hierarchical image database," Presented at 2009 IEEE Conference on Computer Vision and Pattern Recognition, Miami, FL, USA, Jun. 20-25, 2009, pp. 248-255.
distill.pub [online], "Exploring Neural Networks with Activation Atlases," Mar. 6, 2019, retrieved on May 17, 2022, retrieved from URL<https://distill.pub/2019/activation-atlas>, 44 pages.
Eddy, "Accelerated profiled HMM searches," PLoS computational biology, 2011, 16 pages.
Eddy, "Profile hidden Markov models," Bioinformatics, Oct. 1998, 14(9):755-763.
El-Gebali et al., "The Pfam protein families database in 2019," Nucleic acids research, Oct. 2018, 6 pages.
Eraslan et al, "Deep learning: new computational modelling techniques for genomics," Nature Reviews, Jul. 2019, 20:389-403.
Finn et al, "HMMER web server: interactive sequence similarity searching," Nucleic acids research, May 18, 2011, 39:W29-W37.
Finn et al, "The PFAM protein families database: towards a more sustainable future" Nucleic acids research, 2015, 7 pages.
Finn et al., "PFAM: Clans, web tools and services," Nucleic acids research, Jan. 2006, 34(1):D247-D251.
Finn et al., "PFAM: the protein families database," Nucleic acids research, 2013, 9 pages.
github.com [online], "Sufficient Input Subsets," Mar. 8, 2019, retrieved on May 18, 2022, retrieved from URL<https://github.com/b-carter/SufficientInputSubsets>, 2 pages.
Golovin et al., "Google vizier: A service for black-box optimization," Proceedings of the 23rd ACM SIGKDD International Conference on Knowledge Discovery and Data Mining, Aug. 2017, pp. 1487-1495.
Gough et al., "Superfamily: HMMS representing all proteins of known structure scop sequence searches, alignments and genome assignments," Nucleic acids research, Jan. 2002, 30(1):268-272.
Gough et al., "The SUPERFAMILY 2.0 database: a significant proteome update and a new webserver," Nucleic Acids Research, Nov. 2018, 47(D1):D490-D494.
Gueudre et al, "Simultaneous identification of specifically interacting paralogs and interprotein contacts by direct coupling analysis," Proceedings of the National Academy of Sciences, Oct. 25, 2016, 113(43):12186-12191.
Haft et al., "TIGRFAMs and Genome Properties in 2013," Nucleic Acids Res, Jan. 2013, 41:D387-D395.
He et al., "Deep residual learning for image recognition," Proceedings of the IEEE conference on Computer Vision and Pattern Recognition, Jun. 2016, pp. 770-778.
Hochreiter et al, "Long short-term memory," Neural computation, Dec. 1997, 9(8):1735-1780.
Hou et al., "DeepSF: deep convolutional neural network for mapping protein sequences to folds," Bioinformatics, Dec. 2017, 34(8):1295-1303.
Hunter et al., "InterPro: the integrative protein signature database," Nucleic Acids Res, Jan. 2009, 37:D211-D215.
International Preliminary Report on Patentability in International Application No. PCT/US2020/027616, dated Oct. 21, 2021, 16 pages.

(56) References Cited

OTHER PUBLICATIONS

International Search Report and Written Opinion in International Application No. PCT/US2020/027616, dated Sep. 7, 2020, 19 pages.
Invitation to Pay Additional Fees in International Appln. No. PCT/US2020/027616, dated Jul. 8, 2020, 15 pages.
Ioffe et al., "Batch normalization: Accelerating deep network training by reducing internal covariate shift," Proceedings of the 32nd International Conference on Machine Learning, 2015, 9 pages.
Islam et al, "Deepgonet: Multi-label prediction of GO annotation for protein from sequence using cascaded convolutional and recurrent network," arXiv, Oct. 31, 2018, 6 pages.
Kindermans et al, "Learning how to explain neural networks: PatternNet and PatternAttribution," arXiv, Oct. 24, 2017, 12 pages.
Kindermans et al, "The (Un)reliability of saliency methods," arXiv, Nov. 2, 2017, 12 pages.
Kingma et al., "ADAM: A method for stochastic optimization," arXiv, Dec. 22, 2014, 9 pages.
Kirkpatrick et al, "De novo structure prediction with deep-learning based scoring," Casp 13 abstract, 2018, 2 pages.
Kulmanov et al., "DeepGO: Predicting protein functions from sequence and interactions using a deep ontology-aware classifier," Bioinformatics, Oct. 3, 2017, 34(4):660-668.
Lei et al, "Rationalizing Neural predictions," Proceedings of the 2016 Conference on Empirical Methods in Natural Language Processing, Nov. 2016, pp. 107-117.
Li et al, "DEEPre: sequence-based enzyme EC number prediction by deep learning," Bioinformatics, Oct. 23, 2017, 34(5):760-769.
Li et al, "Protein remote homology detection based on bidirectional long short-term memory," BMC bioinformatics, Oct. 10, 2017, 18(1):443, 8 pages.
Liu, "Deep recurrent neural network for protein function prediction from sequence," arXiv, Jan. 28, 2017, 38 pages.
Marks et al, "Protein 3D structure computed from evolutionary sequence variation" PLoS, Dec. 2011, 6(12):e28766, 20 pages.
McCloskey et al, "Using attribution to decode dataset bias in neural network models for chemistry" arXiv, Nov. 29, 2018, 14 pages.
Mi et al., "PANTHER version 10: expanded protein families and functions, and analysis tools," Nucleic Acids Res, Jan. 2016, 44(D1):D336-D342.
Montavon et al, "Methods for interpreting and understanding deep neural networks" Digital Signal Processing, 2018, 20 pages.
Nesterov, "Gradient methods for minimizing composite objective function," Sep. 2007, 31 pages.
Pandit et al., "Supfam: a database of sequence superfamilies of protein domains," BMC bioinformatics, Mar. 15, 2004, 5 pages.
Pascanu et al., "On the difficulty of training recurrent neural networks," ICML, 2013, 9 pages.
Poplin et al., "A universal SNP and small-indel variant caller using deep neural networks," Nature Biotechnology, Sep. 2018, 9 pages.
Price et al., "Mutant phenotypes for thousands of bacterial genes of unknown function," Nature, May 24, 2018, 25 pages.
Rawlings et al., "MEROPS: the peptidase database," Nucleic acids, Jan. 1999, 27(1):325-331.
Ribeiro et al., "Why Should I Trust You?: Explaining the predictions of any classifier," Proceedings of the 22nd ACM SIGKDD International Conference on Knowledge Discovery and Data Mining (KDD '16), Aug. 2016, pp. 1135-1144.
Riesselman et al., "Deep generative models of genetic variation capture the effects of mutations," Nature, Oct. 2018, 15:816-822.
Rose et al., "Web-based molecular graphics for large complexes," Proceedings of the 21st International Conference on Web3D technology, Jul. 2016.
Russakovsky et al., "Imagenet large scale visual recognition challenge," International Journal of Computer Vision, Dec. 2015, 115(3):211-252.
Schaffer et al., "Improving the accuracy of PSI-blast protein database searches with composition-based statistics and other refinements," Nucleic acids research, Jul. 15, 2001, 29(14):2994-3005.
Schuster-Bockler et al., "HMM Logos for visualization of protein families," BMC bioinformatics, Jan. 21, 2004, 8 pages.
Schwartz et al., "Deep semantic protein representation for annotation, discovery, and engineering," bioRxiv, Jul. 10, 2018.
Seo et al., "DeepFam: deep learning based alignment-free method for protein family modeling and prediction," Bioinformatics, 2018, 34(13):i254-i262.
Sha et al., "Interpretable predictions of clinical outcomes with an attention-based recurrent neural network," Proceedings of the 8th ACM International Conference on Bioinformatics, Computational Biology, Aug. 2017, pp. 233-240.
Shrikumar et al., "Learning important features through propagating activation differences," arXiv, Apr. 10, 2017, 9 pages.
Simonyan et al., "Deep inside convolutional networks: Visualising image classification models and saliency maps," arXiv, Dec. 20, 2013, 8 pages.
Smilkov et al., "Tensorflow: Machine learning for the web and beyond," Proceedings of Machine Learning and Systems 1, 2019, 13 pages.
Soding, "Clustering huge protein sequence sets in linear time," Nature communications, 2018, 8 pages.
Soding, "MMSeqs2 enables sensitive protein sequence searching for the analysis of massive data sets," Nature biotechnology, 2017, 3 pages.
Soding, "Protein homology detection by HMM-HMM comparison," Bioinformatics, 2004, 21(7):951-960.
Sonnhammer et al., "PFAM: a comprehensive database of protein domain families based on seed alignments," Proteins: Structure, Function, and Bioinformatics, 1997, 28:405-420.
Springenberg et al., "Striving for simplicity: The all convolutional net," arXiv, Dec. 21, 2014, 12 pages.
Sundararajan et al., "Axiomatic attribution for deep networks," Proceedings of the 34th International Conference on Machine Learning, Aug. 2017, 10 pages.
Szalkai et al., "Near perfect protein multi-label classification with deep neural networks," Methods, 2018, 20 pages.
Tame et al., "The structures of deoxy human haemoglobin and the mutant HB Tyra42His at 120 K," Acta crystallographica section D: biological crystallography, 2000, 7 pages.
The UniProt Consortium, "UniProt: a worldwide hub of protein knowledge," Nucleic Acids Research, 2018, 10 pages.
The UniProt Consortium, "UniProt: the universal protein knowledgebase," Nucleic acids research, Nov. 28, 2016, 45:D158-D169.
Tramer et al., "Stealing machine learning models via prediction APIs," arXiv, Oct. 3, 2016, 19 pages.
Wheeler et al., "Skylign: a tool for creating informative, interactive logos representing sequence alignments and profile hidden Markov models," BMC Bioinformatics, 2014, 9 pages.
Wilson et al., "The marginal value of adaptive gradient methods in machine learning," Advances in Neural Information Processing Systems 30, 2017, 11 pages.
Xu, "Distance-based protein folding powered by deep learning," arXiv, 2018, 16 pages.
Yona et al., "Protomap: automatic classification of protein sequences and hierarchy of protein families," Nucleic acids research, Jan. 2000, 28(1):49-55.
Yu et al., "Multi-scale context aggregation by dilated convolutions," arXiv, Nov. 23, 2015, 9 pages.
Zeiler et al., "Visualizing and understanding convolutional networks," European Conference on Computer Vision, 2014, 16 pages.
Zhou et al., "Learning deep features for discriminative localization," arXiv, Dec. 14, 2015, 10 pages.

* cited by examiner

PREDICTING BIOLOGICAL FUNCTIONS OF PROTEINS USING DILATED CONVOLUTIONAL NEURAL NETWORKS

CROSS-REFERENCE TO RELATED APPLICATION

This application is a National Stage Application under 35 U.S.C. § 371 and claims the benefit of International Application No. PCT/US2020/027616, filed Apr. 10, 2020, which claims priority to U.S. Application No. 62/832,691, filed Apr. 11, 2019, the disclosure of which is incorporated herein by reference.

BACKGROUND

This specification relates to predicting biological functions of proteins using machine learning models.

A protein is specified by a sequence of amino acids. An amino acid is an organic compound which includes an amino functional group and a carboxyl functional group, as well as a side-chain (i.e., group of atoms) that is specific to the amino acid. When in a sequence linked by peptide bonds, the amino acids may be referred to as amino acid residues.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification generally describes a system implemented as computer programs on one or more computers in one or more locations that can predict the biological function of a protein by processing a representation of the amino acid sequence of the protein using a neural network.

As used throughout this specification, the term "protein" may be understood to refer to any biological molecule that is specified by one or more sequences of amino acids. For example, the term protein may be understood to refer to a protein domain (i.e., a portion of an amino acid sequence that can undergo protein folding nearly independently of the rest of the amino acid sequence) or a protein complex (i.e., that is specified by multiple associated amino acid sequences).

According to one aspect there is provided a method performed by one or more data processing apparatus, the method comprising: obtaining data defining a sequence of amino acids in a protein; processing the data defining the sequence of amino acids in the protein using a neural network, wherein: the neural network is a convolutional neural network comprising one or more dilated convolutional layers; and the neural network is configured to process the data defining the sequence of amino acids in the protein in accordance with trained parameter values of the neural network to generate a neural network output characterizing at least one predicted biological function of the sequence of amino acids in the protein; and identifying the predicted biological function of the sequence of amino acids in the protein using the neural network output.

In some implementations, processing the data defining the sequence of amino acids in the protein to generate a neural network output characterizing the predicted biological function of the sequence of amino acids in the protein comprises: generating a respective representation of each amino acid in the sequence of amino acids using the one or more dilated convolutional layers; generating an embedding of the sequence of amino acids in the protein using the respective representation of each amino acid in the sequence of amino acids; and generating the neural network output using the embedding.

In some implementations, generating the embedding of the sequence of amino acids in the protein using the respective representation of each amino acid in the sequence of amino acids comprises pooling the respective representation of each amino acid in the sequence of amino acids.

In some implementations, pooling the respective representation of each amino acid in the sequence of amino acids comprises max-pooling the respective representation of each amino acid in the sequence of amino acids.

In some implementations, generating the neural network output using the embedding comprises: processing the embedding using a dense layer of the neural network; and processing an output of the dense layer using an output layer of the neural network.

In some implementations, the output layer is a sigmoid layer.

In some implementations, the neural network output comprises a respective probability value for each of a plurality of possible biological functions of the sequence of amino acids in the protein.

In some implementations, identifying the predicted biological function of the sequence of amino acids in the protein using the neural network output comprises sampling a possible biological function from the plurality of possible biological functions in accordance with the probability values.

In some implementations, the data defining the sequence of amino acids comprises a one-hot representation of each amino acid in the sequence of amino acids.

In some implementations, one or more of the layers of the neural network are included in residual blocks.

In some implementations, the predicted biological function characterizes chemical reactions the protein is predicted to catalyze.

In some implementations, the predicted biological function comprises an enzyme commission number.

In some implementations, the predicted biological function characterizes a predicted sub-cellular location associated with the protein.

In some implementations, the predicted biological function characterizes a predicted molecular function of the sequence of amino acids in the protein.

In some implementations, the predicted biological function characterizes one or more biological processes to which the sequence of amino acids in the protein is predicted to contribute.

In some implementations, the neural network does not process alignment data characterizing an alignment of the sequence of amino acids in the protein with one or more other sequences of amino acids in other proteins.

In some implementations, the sequence of amino acids corresponds to a domain that is a proper subset of the protein.

In some implementations, the sequence of amino acids corresponds to the entire protein.

In some implementations, each of the dilated convolutional layers are one-dimensional dilated convolutional layers.

In some implementations, the neural network is translationally-invariant.

According to another aspect there is provided a method performed by one or more data processing apparatus, the method comprising: obtaining data defining a plurality of training amino acid sequences that each correspond to a respective protein; generating a respective embedding of each of the plurality of training amino acid sequences, comprising, for each training amino acid sequence: processing the data defining the training amino acid sequence using a neural network that is trained to generate an output that characterizes a predicted biological function of the training amino acid sequence; and identifying the embedding of the training amino acid sequence as an intermediate output generated by the neural network by processing the data defining the training amino acid sequence; and using the embeddings of the plurality of training amino acid sequences to identify a predicted biological function (e.g., a predicted protein family) of a new protein.

In some implementations, using the embeddings of the plurality of training amino acid sequences to identify the predicted biological function (e.g., a predicted protein family) of the new protein comprises: generating an embedding of a new amino acid sequence corresponding to the new protein, comprising: processing data defining the new amino acid sequence using the neural network; and identifying the embedding of the new amino acid sequence as an intermediate output generated by the neural network by processing the data defining the new amino acid sequence; and identifying the predicted biological function (e.g., predicted protein family) of the new protein using: (i) the embeddings of the plurality of training amino acid sequences, and (ii) the embedding of the new amino acid sequence.

In some implementations, identifying the predicted biological function (e.g., predicted protein family) of the new protein using: (i) the embeddings of the plurality of training amino acid sequences, and (ii) the embedding of the new amino acid sequence, comprises: determining, for each of multiple training amino acid sequences, a similarity measure between the embedding of the training amino acid sequence and the embedding of the new amino acid sequence; identifying a particular training amino acid sequence from among the multiple training amino acid sequences based on the determined similarity measures; and identifying the predicted biological function (e.g., predicted protein family) of the new protein as a biological function (e.g., protein family) of the protein corresponding to the particular training amino acid sequence.

In some implementations, identifying the predicted biological function (e.g., predicted protein family) of the new protein using: (i) the embeddings of the plurality of training amino acid sequences, and (ii) the embedding of the new amino acid sequence, comprises: generating a respective embedding corresponding to each of a plurality of biological functions (e.g., protein families) using the embeddings of the plurality of training amino acid sequences; determining, for each of the plurality of biological functions (e.g., protein families), a similarity measure between the embedding corresponding to the biological function (e.g., protein family) and the embedding of the new amino acid sequence; and identifying the predicted biological function (e.g., protein family) of the new protein as a particular biological function (e.g., protein family) from among the plurality of biological functions (e.g., protein families) based on the determined similarity measures.

In some implementations, generating an embedding corresponding to a biological function comprises: identifying one or more training amino acid sequences that correspond to respective proteins having the biological function (e.g., identifying one or more training amino acid sequences that correspond to respective proteins in the protein family); and generating the embedding corresponding to the biological function using the embeddings of the identified training amino acid sequences that correspond to proteins having the biological function.

In some implementations, the method further comprises applying a whitening transformation to the embeddings of the training amino acid sequences and the embedding of the new amino acid sequence prior to identifying the predicted protein family of the new protein.

According to another aspect there is provided a method performed by one or more data processing apparatus, the method comprising: obtaining data defining a plurality of amino acid sequences that each correspond to a respective protein; generating a respective embedding of each of the plurality of amino acid sequences, comprising, for each amino acid sequence: processing the data defining the amino acid sequence using a neural network that is trained to generate an output that characterizes a predicted biological function of the amino acid sequence; and identifying the embedding of the amino acid sequence as an intermediate output generated by the neural network by processing the data defining the amino acid sequence; and determining an assignment of each of the plurality of amino acid sequences to a respective group of amino acid sequences using the embeddings of the plurality of amino acid sequences.

In some implementations, determining an assignment of each of the plurality of amino acid sequences to a respective group of amino acid sequences using the embeddings of the plurality of amino acid sequences comprises clustering the embeddings of the plurality of amino acid sequences.

According to another aspect there is provided a method performed by one or more data processing apparatus, the method comprising: obtaining: (i) a prediction model that is configured to process data defining a sequence of amino acids to generate a prediction output that characterizes the sequence of amino acids, and (ii) data defining a particular sequence of amino acids corresponding to a particular protein; processing the data defining the particular sequence of amino acids using the prediction model to generate a particular prediction output; identifying one or more sensitive positions in the particular sequence of amino acids based on a sensitivity of the particular prediction output to the amino acids in the sensitive positions in the particular sequence of amino acids; presenting a three-dimensional representation of the particular protein that depicts a folding structure of the particular protein and that visually distinguishes the sensitive positions in the particular sequence of amino acids corresponding to the particular protein from positions in the particular sequence of amino acids corresponding to the particular protein that are not sensitive positions.

In some implementations, identifying one or more sensitive positions in the particular amino acid sequence comprises: identifying a proper subset of the positions in the particular sequence of amino acids as sensitive positions based on a measure of similarity between: (i) the particular prediction output generated by the prediction model by processing the data defining the particular sequence of amino acids, and (ii) a prediction output generated by the prediction model by processing data defining the particular sequence of amino acids when the amino acids outside the proper subset of the positions in the particular sequence of amino acids are masked.

According to another aspect there is provided a method performed by one or more data processing apparatus, the method comprising: obtaining: (i) a first prediction model and a second prediction model that are both configured to process data defining a sequence of amino acids to generate a prediction output that characterizes the sequence of amino acids, and (ii) data defining a particular sequence of amino acids; processing the data defining the particular sequence of amino acids using the first prediction model to generate a first prediction output; identifying one or more sensitive positions in the particular sequence of amino acids based on a sensitivity of the first prediction output generated by the first prediction model to the amino acids in the sensitive positions in the particular sequence of amino acids; processing data defining a masked sequence of amino acids using the second prediction model to generate a second prediction output, wherein: the masked sequence of amino acids matches the particular sequence of amino acids at each of the sensitive positions; and the masked sequence of amino acids comprises a masked amino acid at each position that is not a sensitive position; and determining whether the first prediction model and the second prediction model use a same rationale for generating prediction outputs based on a similarity measure between the first prediction output and the second prediction output.

In some implementations, the first prediction model and the second prediction model are both neural network models with a same architecture; and the first prediction mode and the second prediction model are: (i) initialized with different random parameter values, (ii) trained on different sets of training data, or (iii) both.

According to another aspect there is provided a system comprising one or more computers and one or more storage devices storing instructions that when executed by the one or more computers cause the one or more computers to perform the respective operations of any of the previously described methods.

According to another aspect there are provided one or more computer storage media storing instructions that when executed by one or more computers cause the one or more computers to perform the respective operations of any of the previously described methods.

Particular embodiments of the subject matter described in this specification can be implemented so as to realize one or more of the following advantages.

This specification describes a protein function prediction system that can process data defining an amino acid sequence of a protein to predict the biological function of the protein. Some conventional techniques for predicting biological function from amino acid sequence data rely on comparing the amino acid sequence to thousands of models of different protein families, or to even larger databases of individual amino acid sequences using alignment techniques. In contrast, the system described in this specification can, in some examples, directly predict the biological function of an amino acid sequence without comparing the amino acid sequence to other amino acid sequences or protein family models. Therefore, the system may generate biological function predictions more quickly while consuming fewer computational resources (e.g., memory and computing power) than some conventional biological function prediction techniques. Moreover, the system can also generate biological function predictions more accurately than some conventional biological function prediction techniques.

In some examples, the protein function prediction system predicts biological functions of proteins using a neural network that that can process amino acid sequences having any length. That is, the architecture of the neural network does not place any upper bound on the lengths of the amino acid sequences that it can process. The neural network can achieve this length flexibility, e.g., by generating a respective representation (embedding) of each amino acid in an input amino acid sequence, and thereafter combining the amino acid representations into an fixed-dimensionality embedding which is processed by one or more subsequent layers to generate a neural network output. The act of combining amino acid representations into a fixed-dimensionality embedding is referred to here as "pooling". The length flexible architecture of the neural network provides several advantages over possible architectures which are configured to process fixed length amino acid input sequences. For example, in a fixed length architecture, amino acid sequences that are shorter than the fixed length may be padded (e.g., with zeros) until they have the fixed length. For short amino acid sequences, this padding may result in a neural network with a fixed length architecture mainly performing calculations on empty padding. As another example, a fixed length architecture imposes a hard limit on the lengths of amino acid sequences that can be processed.

For certain protein functions, only a limited number of corresponding training examples may be available, i.e., which label particular proteins as performing the function. For example, certain protein functions may have fewer than 100, fewer than 10, or only a single corresponding training example. Some protein function prediction techniques may perform poorly (i.e., have low accuracy) in classifying protein functions for which few training examples are available. This specification describes a protein clustering system that facilitates accurate classification of protein functions for which few training examples are available, and that also enables the identification of novel categories/groups of proteins, as will be described in more detail below.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
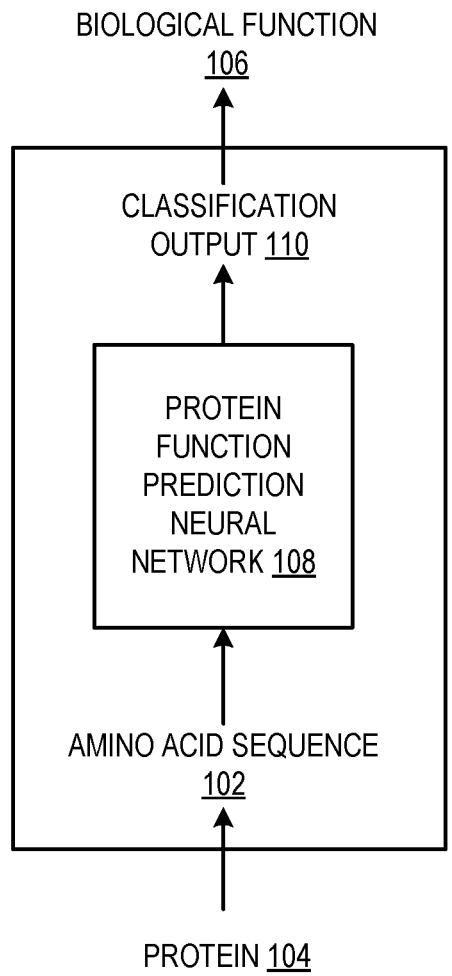
FIG. 1 shows an example protein function prediction system.

FIG. 1 shows an example protein function prediction system 100. The protein function prediction system 100 is an example of a system implemented as computer programs on one or more computers in one or more locations in which the systems, components, and techniques described below are implemented.

The system 100 is configured to process data defining the amino acid sequence 102 of a protein 104 to generate an output that characterizes a predicted biological function 106 of the protein 104. Note that the amino acid sequence 102 may be the whole of the protein 104, or may be a proper subset of the protein 104.

The amino acid sequence 102 can be represented in any appropriate numerical format. For example, the amino acid sequence 102 may be represented as a sequence of one-hot vectors. In this example, each one-hot vector represents a corresponding amino acid in the amino acid sequence 102. A one-hot vector has a different component for each different amino acid (e.g., of a predetermined number of amino acids e.g. 21). A one-hot vector representing a particular amino acid has value one (or some other first predetermined value) in the component corresponding to the particular amino acid and value zero (or some other predetermined value, different from the first predetermined value) in the other components.

The biological function 106 specifies one or more biological functions that are associated with the protein 104.

For example, the biological function 106 may specify a chemical reaction that is catalyzed by the protein 104, e.g., by specifying an enzyme commission (EC) number of the protein 104. In a particular example, the EC number "EC 3.4" may indicate that the protein is a hydrolase that catalyzes hydrolysis of peptide bonds.

As another example, the biological function 106 may specify a sub-cellular location associated with the protein, e.g., the nucleus, the endoplasmic reticulum, or the Golgi apparatus. A protein may be associated with a particular sub-cellular location if the protein is frequently present at the particular sub-cellular location.

As another example, the biological function 106 may characterize one or more biological processes to which the protein 104 is predicted to contribute, e.g., cell growth and maintenance, and cellular signaling and communication.

As another example, the biological function 106 may specify a corresponding protein family, i.e., a collection of evolutionarily-related proteins that have the same one or more functions (or one or more functions which collectively meet a similarity criterion).

To identify the biological function 106 of the protein 104, the system 100 processes data defining the amino acid sequence 102 using a protein function prediction neural network 108 to generate a classification output 110, and then identifies the biological function 106 based on the classification output 110.

The classification output 110 may include a respective score corresponding to each of multiple possible biological functions, where the score corresponding to a given function characterizes a likelihood (e.g., a probability) that the protein 104 has the given function. In some implementations, the system 100 may identify the biological function 106 of the protein 104 as the possible biological function having the highest corresponding score (i.e., according to the classification output 110). In some implementations, the system 100 may identify each possible biological function having a score that satisfies a threshold as being a biological function 106 of the protein 104. In these implementations, the system 100 may identify multiple biological functions 106 of the protein, e.g., if the respective score associated with multiple possible biological functions each satisfy the threshold. In some implementations, the system 100 may identify the biological function 106 of the protein 104 by sampling a possible biological function in accordance with a probability distribution over the set of possible biological functions that is specified by the scores.

An example architecture of the protein function prediction neural network 108 is described in more detail with reference to FIG. 2.

The system 100 may train the protein function prediction neural network 108 on a set of training data that includes multiple training examples. Each training example may specify: (i) a training amino acid sequence, and (ii) a target classification output that should be generated by the neural network 108 by processing the training amino acid sequence. The system 100 may train the neural network 108 on the training data to optimize an appropriate loss function, e.g., a cross entropy loss function, using an appropriate machine learning training technique, e.g., stochastic gradient descent.

Biological function predictions generated by the protein function prediction system 100 (or the protein clustering system, which will be described in more detail below) can be used for any of a variety of purposes. For example, the biological function predictions can be used to identify disease mechanisms, e.g., to understand the effects of a disease that inhibits folding of a particular protein in the body. As another example, the biological function predictions can be used to facilitate drug discovery, e.g., to identify proteins that perform a specific function in the body, such that a drug comprising the protein could be administered to a patient to achieve a therapeutic effect. As another example, industrial processes may use proteins as part of synthesizing compounds for use in, e.g., pharmaceuticals or fertilizers, and the biological function predictions may facilitate the discovery of new compounds, optimize the synthesis of existing compounds, or both.

Figure 2:
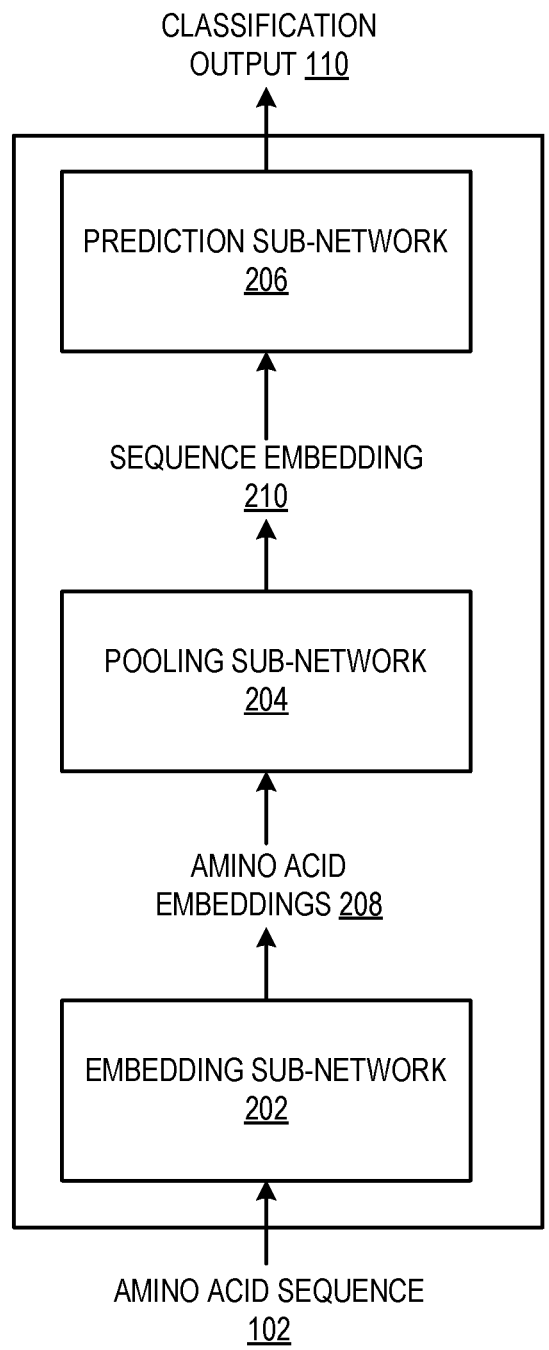
FIG. 2 shows an example architecture of a protein function prediction neural network.

FIG. 2 shows an example architecture of a protein function prediction neural network 108. The neural network 108 is configured to process data defining an amino acid sequence 102 of a protein to generate a classification output 110 that includes a respective score corresponding to each of multiple possible biological functions, as described above.

The neural network 108 includes an embedding sub-network 202, a pooling sub-network 204, and a prediction sub-network 206, which will each be described in more detail next. As used throughout this specification, a "sub-network" of a neural network may refer to a collection of one or more neural network layers that are included in a neural network.

The embedding sub-network 202 processes data defining the amino acid sequence 102 to generate a respective embedding 208 of each amino acid in the amino acid sequence 102. The amino acid sequence 102 may be defined, e.g., by a respective one-hot vector corresponding to each amino acid in the amino acid sequence 102. As used throughout this specification, an "embedding" refers to an ordered collection of numerical values having a fixed number of numerical values, e.g., a vector or matrix of numerical values.

Each neural network layer of the embedding sub-network 202 may be configured to: (i) receive a respective current embedding of each amino acid in the sequence 102, and (ii) update the respective current embedding of each amino acid in the sequence 102. A neural network layer of the embedding sub-network 202 may update the current embeddings by processing the current embeddings in accordance with current values of a set of layer parameters, e.g., by applying a dilated convolution operation to the current embeddings, as will be described in more detail below. The amino acid embeddings of the amino acids in the sequence 102 that are provided as inputs to the input layer of the embedding sub-network 202 may be one-hot embeddings.

In some implementations, the embedding sub-network 202 may include one or more "dilated" convolutional neural network layers. Generally, a convolutional layer generates a layer output by convolving one or more kernels with the layer input (a "kernel" may be defined by an ordered collection of numerical values, e.g., a vector of numerical values). In a dilated convolutional layer, the convolution operation skips inputs (i.e., components of the layer input) according to a step size referred to as the dilation rate. Different dilated convolutional layers within the embedding sub-network 202 may have different dilation rates. The dilation rates of dilated convolutional layers of the embedding sub-network 202 may be doubled every dilated convolutional layer, starting from a dilation rate of 1. The dilated convolutional layers of the embedding sub-network 202 may be one-dimensional (1-D) convolutional layers such that the convolution operation applied to the layer inputs is a 1-D convolution operation (i.e., where convolutional kernels "slide" along a layer input in only one dimension). Optionally, the layer input to a convolutional layer may be padded with default values (e.g., zeros) to facilitate computation of the convolution operation in instances where the kernel extends beyond the original layer input.

Using dilated convolutional layers may enable the embedding sub-network 202 to achieve larger receptive field sizes than would be achieved by using non-dilated convolutional layers. The receptive field size of a neuron in the embedding sub-network 202 may characterize the length of the subsequence of the amino acid sequence 102 that affects the input provided to the neuron. Having larger receptive fields enables the embedding sub-network 202 to generate more informative amino acid embeddings 208, e.g., such that the embedding of each amino acid in the sequence 102 incorporates information from across a larger portion of the amino acid sequence 102, and thereby achieve greater prediction accuracy.

In some implementations, the embedding sub-network 202 may include one or more residual blocks. A residual block may refer to a collection of one or more neural network layers where the output of the block is a combination (e.g., sum) of: (i) the input to the first layer in the block, and (ii) the output of the last layer in the block. Using residual blocks may facilitate more effective training of the neural network 108, e.g., by enabling faster training, and by causing the training to be more stable.

An example architecture of the embedding sub-network 202 is described in more detail with reference to FIG. 3.

The pooling sub-network 204 processes the amino acid embeddings 208 of the amino acids in the amino acid sequence 102 to generate a sequence embedding 210 of the entire amino acid sequence 102. The pooling sub-network 204 may implement a pooling operation (e.g., by a pooling neural network layer) that is independent of the ordering of the amino acid embeddings 208 and that generates a fixed-dimensionality sequence embedding 210, i.e., that is independent of the length of the amino acid sequence 102. For example, the pooling sub-network 204 may implement a max-pooling operation (i.e., that defines each component of the sequence embedding 210 to be the maximum of the corresponding components of the amino acid embeddings 208) or an average pooling operation (i.e., that averages the amino acid embeddings 208).

The prediction sub-network 206 processes the sequence embedding 210 of the amino acid sequence 102 to generate the classification output 110. In one example, to generate the classification output 110, the prediction sub-network 206 may process the sequence embedding 210 using a dense (i.e., fully-connected) neural network layer followed by an output layer. The output layer may apply a non-linear activation function, e.g., a soft-max function or a sigmoid function, to the output of the dense layer.

By generating a respective embedding 208 of each amino acid in the amino acid sequence 102 using convolutional layers and combining the amino acid embeddings 208 to generate a fixed-dimensionality sequence embedding 210, the neural network 108 can process amino acid sequences having any length. That is, the architecture of the neural network 108 does not place any upper bound on the lengths of the amino acid sequences that can be processed. More specifically, each convolutional layer of the embedding sub-network may process a layer input that includes an arbitrary number of amino acid embeddings, and the pooling sub-network subsequently projects the arbitrary number of amino acid embeddings output by the embedding sub-network to a fixed-dimensionality sequence embedding. The fixed-dimensionality sequence embedding may thereafter be processed by the prediction sub-network. The "length" of an amino acid sequence may refer to the number of amino acids in the amino acid sequence. The fixed-dimensionality of the sequence embedding 210 may be equal to the dimensionality of each respective amino acid embedding 208.

In addition to being length-flexible, the neural network 108 may further be "translationally-invariant", i.e., such that applying a translation operation to an amino acid sequence 102 may, in some cases, not affect the classification output generated by the neural network 108 by processing the amino acid sequence 102. A translation operation may refer to shifting each amino acid in the sequence forwards or backwards by a fixed number of positions.

Optionally, the neural network 108 may process other inputs in addition to the amino acid sequence 102. For example, the neural network 108 may process data defining a multiple sequence alignment (MSA) corresponding to the amino acid sequence 102, or features derived from the MSA. An MSA specifies a sequence alignment of the amino acid sequence 102 with multiple additional amino acid sequences, e.g., from other proteins. An MSA may be generated, e.g., by processing a database of amino acid sequences using any appropriate computational sequence alignment technique, e.g., progressive alignment construction. The amino acid sequences in an MSA may be understood as having an evolutionary relationship, e.g., where each amino acid sequence in the MSA may share a common ancestor. The correlations between the amino acid sequences in the MSA may encode information that is relevant to predicting protein function. Note, however, that some embodiments do not process alignment data. That is, they predict the biological function of an amino acid sequence 102 without comparing the amino acid sequence to other amino acid sequences.

Figure 3:
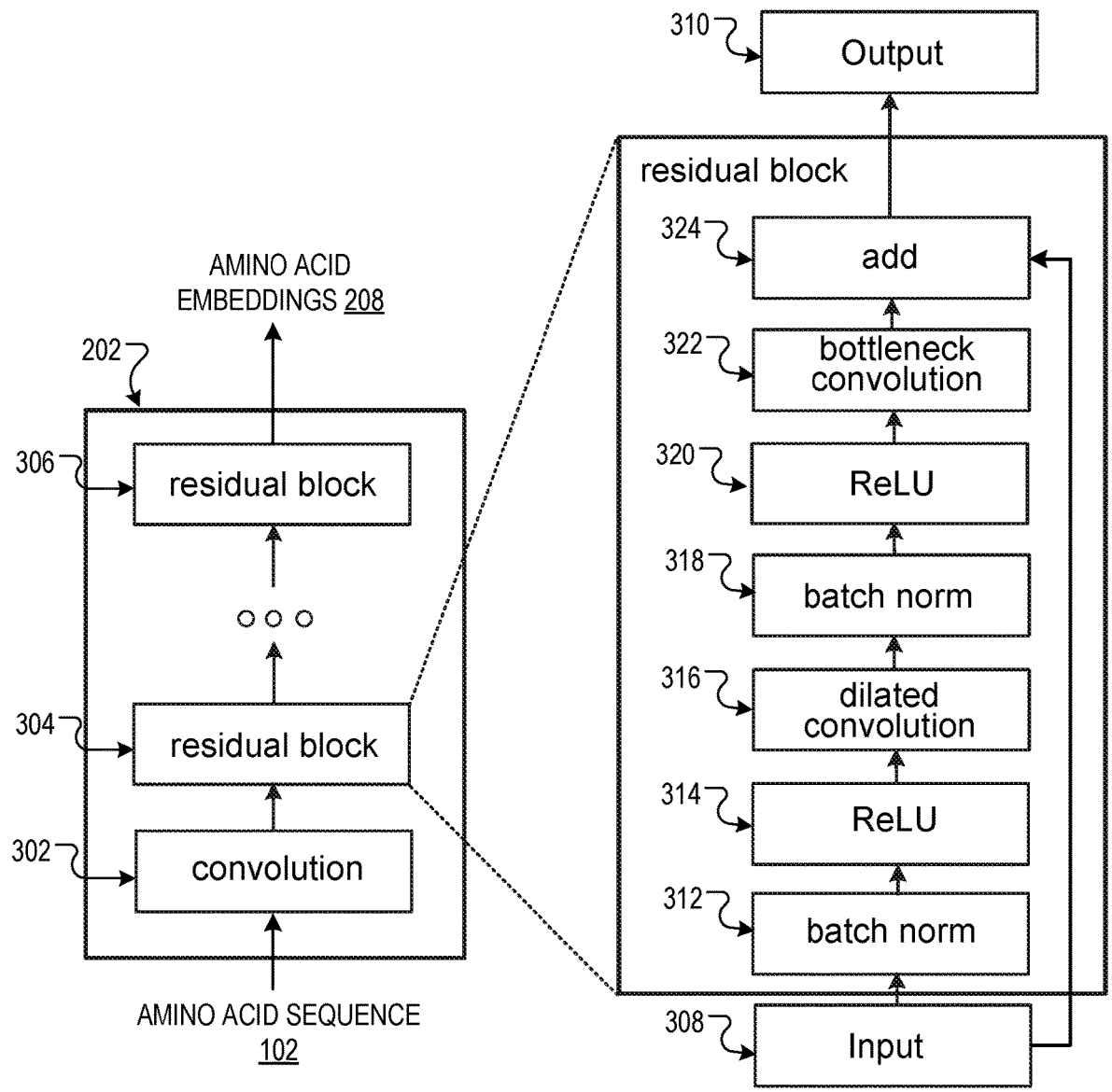
FIG. 3 shows an example architecture of an embedding sub-network of a protein function prediction neural network.

FIG. 3 shows an example architecture of an embedding sub-network 202 of a protein function prediction neural network. The embedding sub-network 202 is configured to process data defining an amino acid sequence 102 to generate a respective embedding 208 of each amino acid in the amino acid sequence 102.

The embedding sub-network 202 includes an initial convolutional neural network layer 302 followed by a sequence of multiple residual blocks (e.g., 304 and 306). The final residual block 306 outputs the amino acid embeddings 208.

Each residual block is configured to receive an input 308 that includes a current embedding of each amino acid in the sequence 102, and to generate an output 310 that updates the current embedding of each amino acid in the sequence 102. Each residual block includes a sequence of neural network layers, and performs a sequence of operations including: a batch normalization operation 312, a rectified linear unit (ReLU) activation function operation 314, a 1-D dilated convolutional operation 316 (as described above), a batch normalization operation 318, a ReLU activation function operation 320, a 1-D bottleneck convolution operation 322 (e.g., that reduces the dimensionality of each current amino acid embedding), and an addition operation 324 (i.e., to add the input 308 to the residual block to the output of the bottleneck convolution operation 322).

Figure 4:
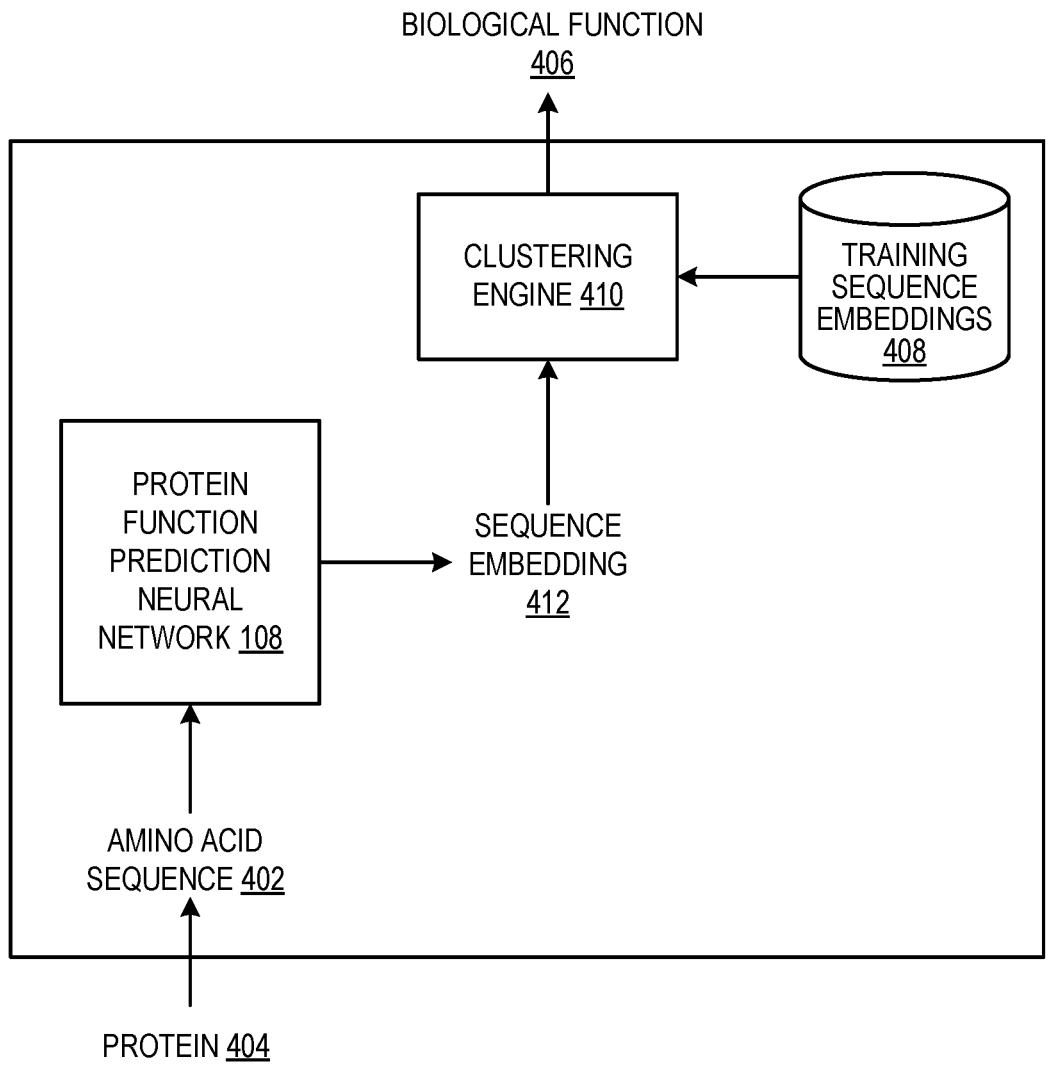
FIG. 4 shows an example protein clustering system.

FIG. 4 shows an example protein clustering system 400. The protein clustering system 400 is an example of a system implemented as computer programs on one or more computers in one or more locations in which the systems, components, and techniques described below are implemented.

The protein clustering system 400 is configured to process data defining the amino acid sequence 402 of a protein 404 to generate an output that characterizes a predicted biological function 406 of the protein 404.

For certain protein functions, only a limited number of corresponding training examples may be available, i.e., which label particular proteins as performing the function. For example, certain protein functions may have fewer than 100, fewer than 10, or only a single corresponding training example. A protein function prediction neural network (as described with reference to FIG. 1) may perform poorly (i.e., have low accuracy) in classifying protein functions for which few training examples are available. The protein clustering system 400 facilitates accurate classification of protein functions for which few training examples are available, as will be described in more detail below.

The protein clustering system 400 includes a protein function prediction neural network 108, a set of training sequence embeddings 408, and a clustering engine 410, which will each be described in more detail next.

The protein function prediction neural network 108 is trained to process data defining the amino acid sequence of a protein to generate an output that characterizes a predicted biological function of the protein. For example, the neural network 108 may be trained to process a representation of an amino acid sequence as a sequence of one-hot embeddings to generate an output that includes a respective score corresponding to each biological function in a set of "baseline" biological functions. An example architecture of a protein function prediction neural network is described in more detail with reference to FIG. 2 and FIG. 3.

In processing a representation of an amino acid sequence of a protein to generate an output characterizing a predicted biological function of the protein, the neural network 108 may generate an intermediate output referred to as a sequence embedding 412. An intermediate output of a neural network refers to an output generated by one or more intermediate (hidden) layers of the neural network. In one example, the sequence embedding 412 may be an intermediate output generated by the pooling sub-network 204 of the neural network 108, as described with reference to FIG. 2. Generally, the sequence embedding 412 is fixed-dimensionality embedding of the amino acid sequence 402, i.e., an embedding having a dimensionality that is independent of the number of amino acids in the sequence 402. The sequence embedding 412 of an amino acid sequence 402 of a protein 404 may implicitly characterize various features of the protein 404 that are relevant to classifying its function.

The set of training sequence embeddings 408 includes a respective sequence embedding (i.e., generated as an intermediate output of the neural network 108) corresponding to each of multiple training amino acid sequences, i.e., for which the associated biological function is known. Generally, the set of training sequence embeddings 408 may include sequence embeddings that are associated with biological functions which are not included in the set of baseline biological functions that the neural network 108 is trained to classify. A biological function may not be included in the set of baseline biological functions that the neural network is trained to classify, e.g., because few training examples corresponding to the biological function are available, and therefore training the neural network 108 to effectively classify the biological function may be impracticable.

To identify the predicted biological function 406 of a protein 404, the protein clustering system 400 processes the protein 404 using the neural network 108 to generate a sequence embedding 412 corresponding to the protein, and then provides the sequence embedding 412 to the clustering engine 410. The clustering engine 410 is configured to identify the biological function 406 of the protein 404 based on: (i) the sequence embedding 412 of the protein 404, and (ii) the set of training sequence embeddings 408. A few example implementations of the clustering engine 410 are described in more detail next.

In one implementation, the clustering engine 410 may determine a respective similarity measure between the sequence embedding of the protein 404 and each training sequence embedding 408, and thereafter identify the biological function 406 of the protein 404 based on the similarity measures. The clustering engine 410 may determine the similarity measure between two sequence embeddings, e.g., as a Euclidean similarity measure, a cosine similarity measure, or as any other appropriate numerical similarity measure. In one example, the clustering engine 410 may identify the protein 404 as having the biological function associated with the "closest" training sequence embedding 408, i.e., the training sequence embedding 408 having the highest similarity to the sequence embedding 412 of the protein 404. In another example, to identify the biological function 406 of the protein 404, the clustering engine 410 may identify a predefined number n>1 of "neighboring" training sequence embeddings 408 that are closest to the sequence embedding 412 of the protein 404. In this example, the clustering engine 410 may identify the protein 404 as having the biological function that is most common among the neighboring training sequence embeddings.

In another implementation, the clustering engine 410 may process the training sequence embeddings 408 to generate a respective embedding corresponding to each of multiple biological functions. To generate the embedding corresponding to a biological function, the clustering engine 410 may aggregate (e.g., average, or otherwise combine) the training sequence embeddings that are associated with the biological function. The clustering engine 410 may determine a respective similarity measure between the sequence embedding 412 of the protein 404 and each biological function embedding, and thereafter identify the biological function 406 of the protein 404 based on the similarity measures. For example, the clustering engine 410 may identify the protein 404 as having the biological function associated with the closest biological function embedding.

Optionally, the clustering engine 410 may apply one or more transformations (e.g., a whitening transformation) to the training sequence embeddings 408 and the sequence embedding of the protein 404 prior to predicting the biological function 406.

The clustering engine 410 may enable the protein clustering system 400 to effectively classify proteins having biological functions that are not included in the set of baseline biological functions that the neural network 108 is trained to classify. Sequence embeddings generated by the neural network 108 may implicitly characterize various protein properties, e.g., stability, structural disorder, presence of transmembrane helical domains, and the like. Proteins having the same function, including a function outside the set of baseline functions the neural network 108 is trained to classify, are more likely to be co-located in the sequence embedding space, i.e., to have similar sequence embeddings. This property may enable the protein clustering system 400 to effectively classify the biological functions of proteins, even for biological functions with few associated training examples, by comparing the proximity of protein sequence embeddings generated by the neural network 108.

In addition to facilitating protein function prediction, the protein clustering system 400 may use sequence embeddings 412 generated as intermediate outputs of the neural network 108 to identify novel categories/groups of proteins. For example, the protein clustering system 400 may generate a respective sequence embedding 412 corresponding to each protein in a collection of proteins, and use the sequence embeddings to assign each protein to a respective group of proteins, e.g., by clustering the sequence embeddings. The protein clustering system 400 may cluster the sequence embeddings using any appropriate clustering algorithm, e.g., a k-means or expectation maximization clustering algorithm. The parameters of the clustering algorithm (e.g., the number of clusters to be identified) may be varied to generate protein groupings having different characteristics and properties. Groups of proteins that are identified by clustering protein sequence embeddings may be used in a variety of practical applications, e.g., drug discovery. In one example, after identifying a given protein having certain desirable characteristics (e.g., therapeutic effects), other proteins in a same cluster as the given protein may be identified as candidates for further research and investigation.

Figure 5:
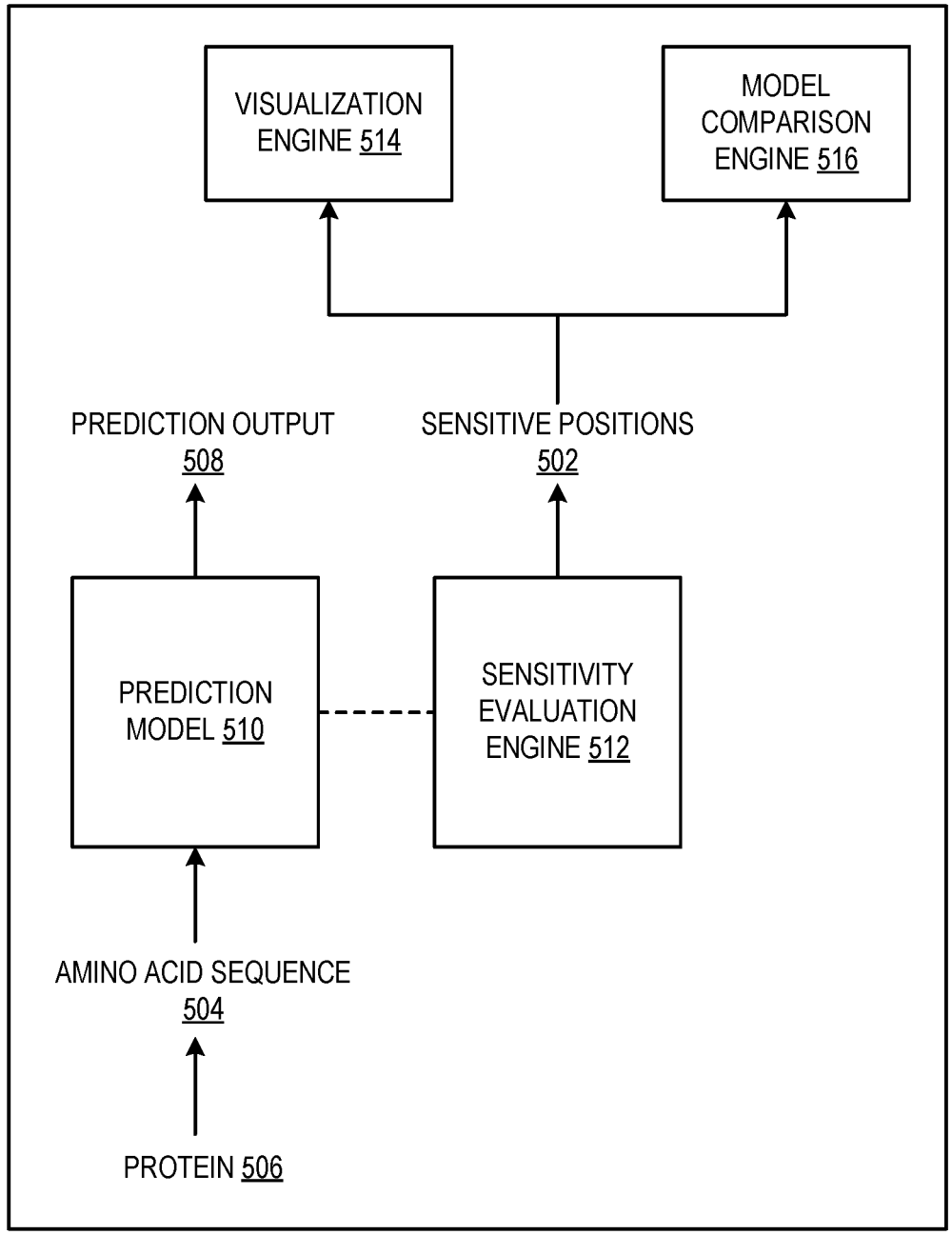
FIG. 5 shows an example sensitivity analysis system.

FIG. 5 shows an example sensitivity analysis system 500. The sensitivity analysis system 500 is an example of a system implemented as computer programs on one or more computers in one or more locations in which the systems, components, and techniques described below are implemented.

The sensitivity analysis system 500 uses a sensitivity evaluation engine 512 to identify a set of one or more "sensitive" positions 502 in an amino acid sequence 504 of a protein 506. The sensitive positions 502 are a proper subset of the positions in the amino acid sequence 504 that significantly affect a prediction output 508 generated by a prediction model 510 by processing the amino acid sequence 504. The sensitivity analysis system 500 may provide the sensitive positions 502 as inputs to a visualization engine 514, a model comparison engine 516, or both, as will be described in more detail below.

The sensitivity evaluation engine 512 may identify a set of sensitive positions 502 having the property that the prediction model 510 generates the same prediction output 508 after amino acids at positions outside the set of sensitive positions are "masked". Masking the amino acid at a given position in the amino acid sequence may refer to setting the identity of the amino acid at the given position to another value, such as a default (i.e., predefined) value, having the effect of removing the information represented by the amino acid at the given position. The sensitive positions 502 may represent information that is sufficient for the prediction model 510 to generate the prediction output 508, even in the absence of the information represented by positions in the amino acid sequence 504 that are outside the set of sensitive positions 502.

Two prediction outputs may be referred to as being the "same" if a measure of similarity between them satisfies a threshold. In one example, the prediction model 510 may be a protein function prediction neural network and the prediction output 508 may be a classification output (as described with reference to FIG. 1). In this example, the sensitivity evaluation engine 512 may identify two classification outputs as being the same if both classification outputs assign a score to a same protein function that satisfies (e.g., exceeds) a threshold (e.g., 0.90).

The sensitivity evaluation engine 512 may identify the set of sensitive positions 502 in the amino acid sequence 504 in any of a variety of ways. Example techniques that can be applied to identify sensitive positions in the amino acid sequence 504 are described in: Carter, B., et al.: "What made you do this? Understanding black-box decisions with sufficient input subsets," arXiv:1810.03805v2, 2019. Identifying the sensitive positions 502 may include generating a masked representation of the amino acid sequence 504, and computing a similarity measure between the respective prediction outputs generated for: (i) the original amino acid sequence, and (ii) the masked amino acid sequence. The sensitivity evaluation engine 512 may represent a masked amino acid sequence as a sequence of vectors that includes a respective one-hot vector representing the amino acid in each unmasked position, and a default vector representing the amino acid in each masked position. The default vector may be, e.g., a vector with all zero values.

Generally, identifying sensitive positions 502 in the amino acid sequence 504 may facilitate understanding of the decision-making criteria employed by the prediction model 510 to generate the prediction output 508. For example, the visualization engine 514 may process the sensitive positions to generate a 3-D representation of the folded structure of a protein, where the sensitive positions in the amino acid sequence of the protein are visually distinguished from the remaining positions. An example output of the visualization engine 514 is illustrated with reference to FIG. 6, which is described in more detail below. As another example, the model comparison engine 516 may process sensitive positions generated by the sensitivity evaluation engine 512 to determine whether two prediction models use the same rationale for generating prediction outputs. Example operations that can be performed by the model comparison engine 516 are described in more detail below with reference to FIG. 7.

Figure 6:
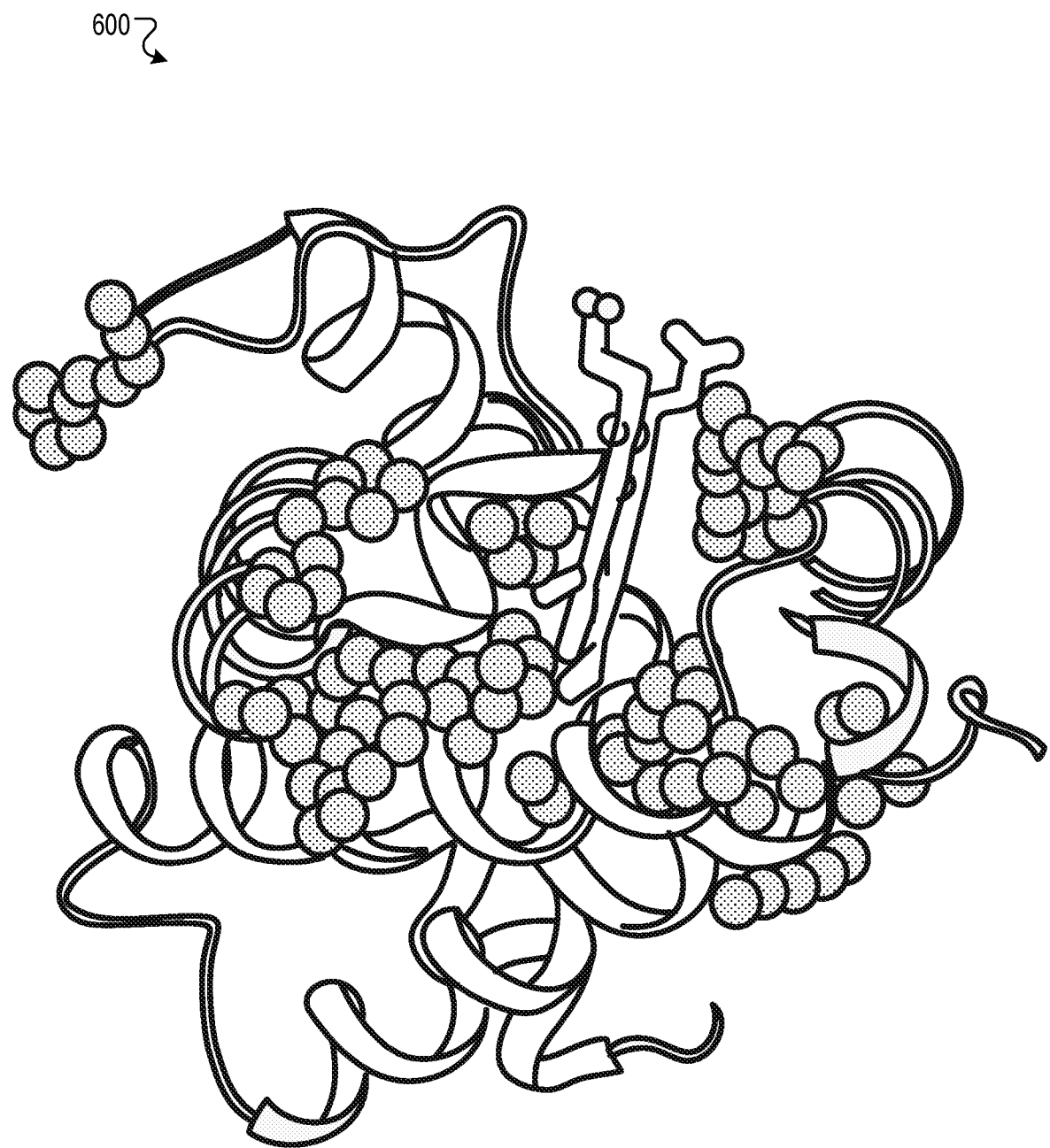
FIG. 6 illustrates a 3-D representation of the structure of a folded protein, where sensitive positions in the amino acid sequence of the protein are rendered as spheres.

FIG. 6 illustrates a 3-D representation 600 of the structure of a folded protein, e.g., that may be generated by the visualization engine 514 described with reference to FIG. 5, where sensitive positions in the amino acid sequence of the protein are rendered as spheres. The 3-D representation of the protein may be presented to a user, e.g., through a visual display of a user device, to facilitate understanding of the decision-making criteria employed by a prediction model that processes the protein to generate a prediction output.

Figure 7:
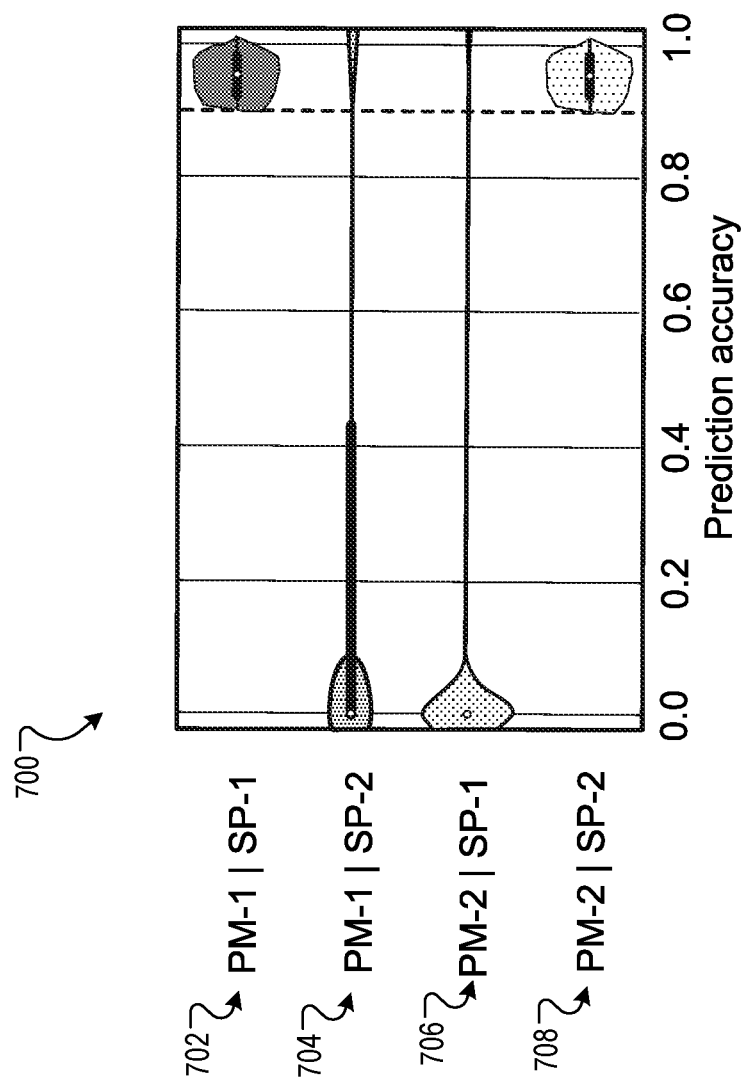
FIG. 7 shows a plot that illustrates the prediction accuracy of two prediction models.

FIG. 7 shows a plot 700 that illustrates the prediction accuracy of two prediction models—"PM-1" and "PM-2"—on two sets of training examples—"SP-1" and "SP-2". Each prediction model (which may have the structure illustrated in FIG. 1) is configured to process an amino acid sequence to generate a corresponding prediction output. Each training example includes: (i) an amino acid sequence, and (ii) a target output that should be generated by processing the amino acid sequence. In the set of training examples SP-1, each amino acid sequence is masked such that each position outside a set of sensitive positions for the amino acid sequence, determined with reference to PM-1, is masked. In the set of training examples SP-2, each amino acid sequence is masked such that each position outside a set of sensitive positions for the amino acid sequence, determined with reference to PM-2, is masked. The sensitive positions in an amino acid sequence may be identified by the sensitivity evaluation engine described with reference to FIG. 5.

The plot 700 illustrates the prediction accuracy of: (i) prediction model PM-1 on training examples SP-1 (702), (ii) prediction model PM-1 on training examples SP-2 (704), (iii) prediction model PM-2 on training examples SP-1 (706), and (iv) prediction model PM-2 on training examples SP-2 (708). In the present example, both PM-1 and PM-2 are protein function prediction neural networks having the same architecture, but that are each: (i) initialized with different random parameter values, (ii) trained on different sets of training data, or (iii) both. It can be appreciated that PM-1 achieves high accuracy for SP-1 but low accuracy for SP-2, and that PM-2 achieves high accuracy for SP-2 but low accuracy for SP-1, which suggests that PM-1 and PM-2 are generating prediction outputs using different decision-making criteria. The data represented by the plot 700 may be generated by the model comparison engine 516 described with reference to FIG. 5.

The model comparison engine 516 described with reference to FIG. 5 may also directly compare prediction outputs generated by a first prediction model and a second prediction model to assess whether the first prediction model and the second prediction model use the same rationale for generating prediction outputs. For example, an amino acid sequence may be processed by the first prediction model to generate a corresponding prediction output, and thereafter a set of sensitive positions may be determined for the amino acid sequence with reference to the first prediction model. The amino acid sequence may then be masked, in particular, by masking positions in the amino acid sequence that are outside the set of sensitive positions, and the masked amino acid sequence may be processed by the second prediction model to generate a corresponding prediction output. A similarity measure may then be computed between the respective prediction outputs generated by the first and second prediction models. Greater similarity between the prediction outputs generated by the first and second prediction models may suggest that the first and second prediction models use similar rationales in generating prediction outputs. The similarity measure may be, e.g., a Euclidean similarity measure, or any other appropriate similarity measure.

The results of comparing the rationales used by different prediction models in generating prediction outputs may guide a user in assessing how to use prediction outputs generated by the prediction models. For example, in response to determining that different prediction models use substantially different rationales for generating prediction outputs, a user may determine that greater reliability and accuracy may be achieved by averaging (or otherwise aggregating) prediction outputs generated by the different prediction models.

Figure 8:
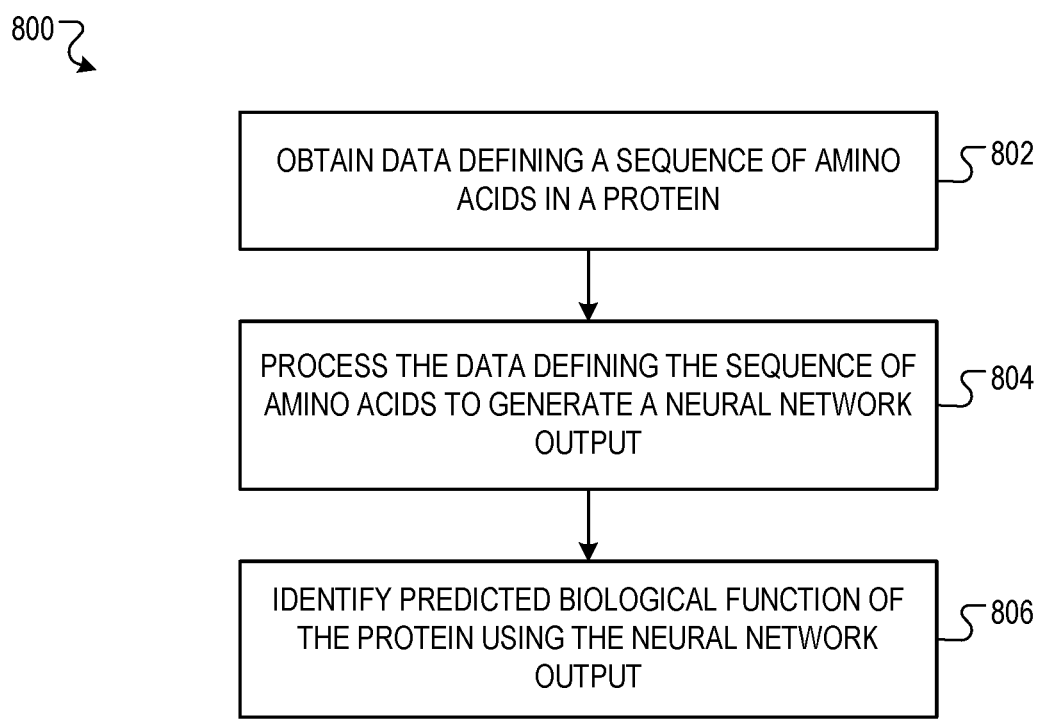
FIG. 8 is a flow diagram of an example process for identifying a predicted biological function of a sequence of amino acids of a protein using a protein function prediction neural network.

FIG. 8 is a flow diagram of an example process 800 for identifying a predicted biological function of a sequence of amino acids of a protein using a protein function prediction neural network. For convenience, the process 800 will be described as being performed by a system of one or more computers located in one or more locations. For example, a protein function prediction system, e.g., the protein function prediction system 100 of FIG. 1, appropriately programmed in accordance with this specification, can perform the process 800.

The system obtains data defining a sequence of amino acids in a protein (802).

The system processes the data defining the sequence of amino acids in the protein using a neural network, in accordance with trained parameter values of the neural network, to generate a neural network output characterizing the predicted biological function (804). The neural network may be a convolutional neural network that includes one or more dilated convolutional layers.

The system identifies the predicted biological function of the sequence of amino acids in the protein using the neural network output (806).

Figure 9:
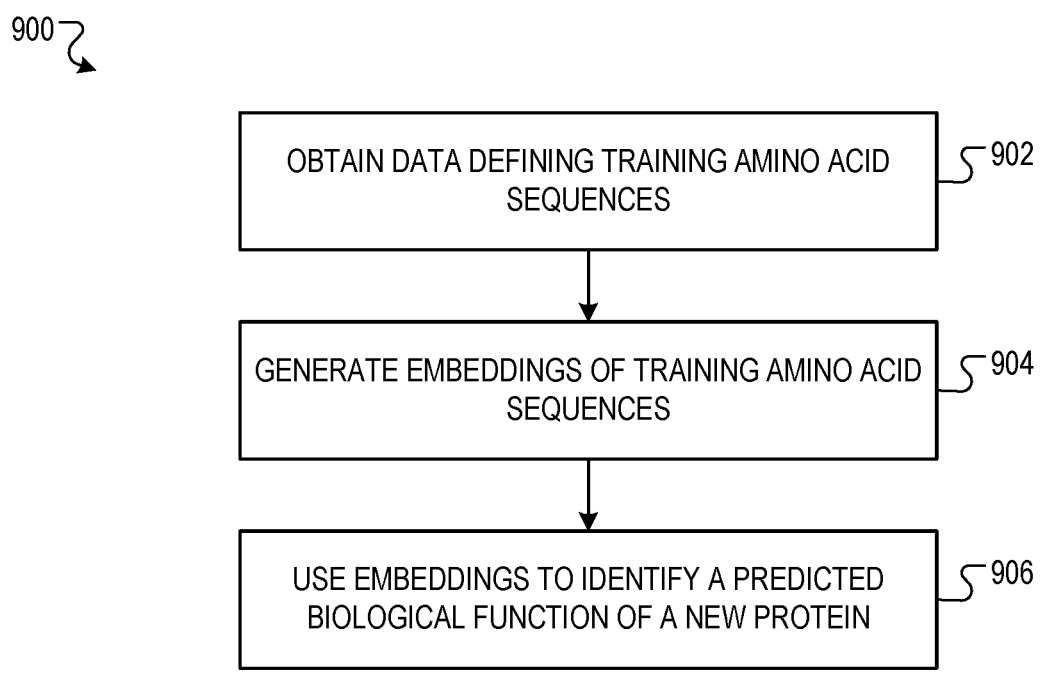
FIG. 9 is a flow diagram of an example process for identifying a predicted biological function of a new protein using embeddings of a set of training amino acid sequences.

FIG. 9 is a flow diagram of an example process 900 for identifying a predicted biological function of a new protein using embeddings of a set of training amino acid sequences. For convenience, the process 900 will be described as being performed by a system of one or more computers located in one or more locations. For example, a protein clustering system, e.g., the protein clustering system 400 of FIG. 4, appropriately programmed in accordance with this specification, can perform the process 900.

The system obtains data defining a set of training amino acid sequences that each correspond to a respective protein (902).

The system generates a respective embedding of each of the training amino acid sequences (904). The system may process data defining each training amino acid sequence using a neural network that is trained to generate an output that characterizes a predicted biological function of the training amino acid sequence. The system may identify the embedding of each training amino acid sequence as an intermediate output generated by the neural network by processing the data defining the training amino acid sequence.

The system uses the embeddings of the training amino acid sequences to identify a predicted biological function of the new protein (906).

Figure 10:
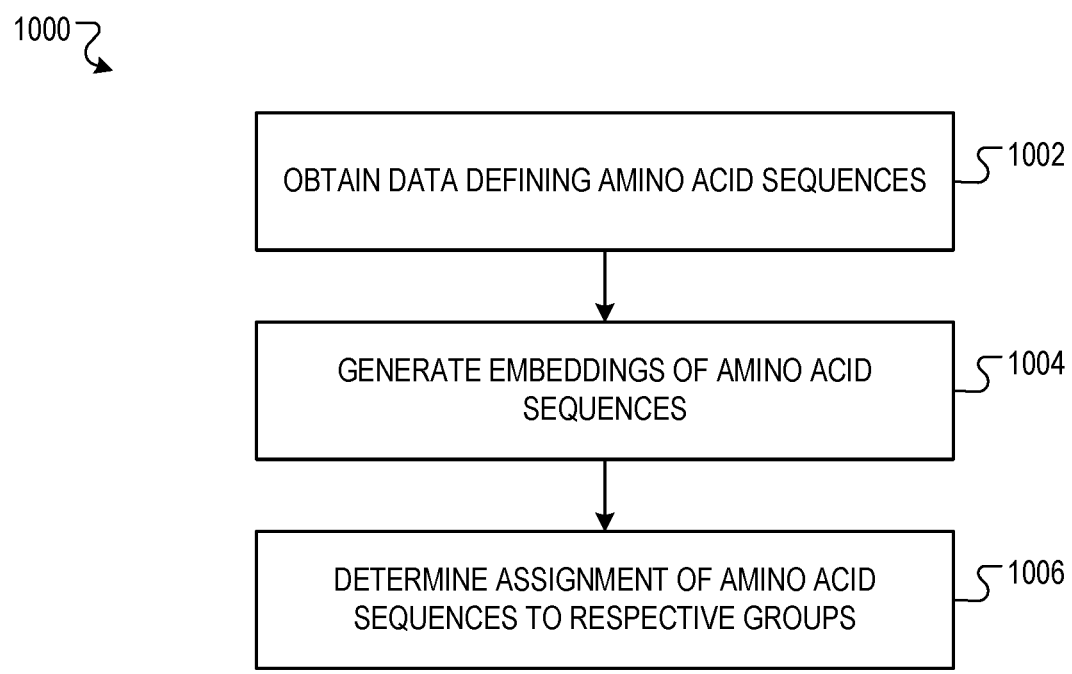
FIG. 10 is a flow diagram of an example process for grouping amino acid sequences.

FIG. 10 is a flow diagram of an example process 1000 for grouping amino acid sequences. For convenience, the process 1000 will be described as being performed by a system of one or more computers located in one or more locations. For example, a protein clustering system, e.g., the protein clustering system 400 of FIG. 4, appropriately programmed in accordance with this specification, can perform the process 1000.

The system obtains data defining a set of amino acid sequences that each correspond to a respective protein (1002).

The system generates a respective embedding of each of the amino acid sequences (1004). The system processes data defining each amino acid sequence using a neural network that is trained to generate an output that characterizes a predicted biological function of the amino acid sequence. The system identifies the embedding of each amino acid sequence as an intermediate output generated by the neural network by processing the data defining the amino acid sequence.

The system determines an assignment of each of the amino acid sequences to a respective group of amino acid sequences using the embeddings of the amino acid sequences (1006).

Figure 11:
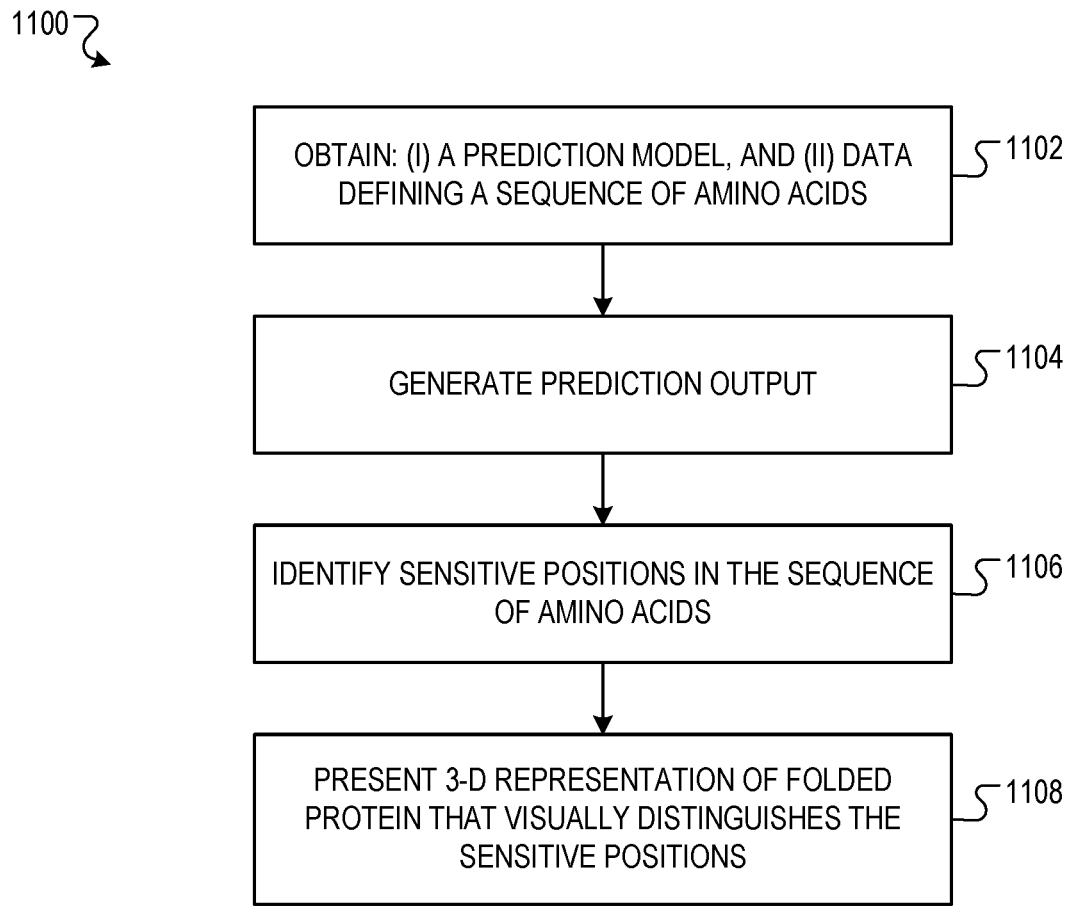
FIG. 11 is a flow diagram of an example process for presenting a 3-D representation of the folding structure of a protein that visually distinguishes sensitive positions in the amino acid sequence of the protein.

FIG. 11 is a flow diagram of an example process 1100 for presenting a 3-D representation of the folding structure of a protein that visually distinguishes sensitive positions in the amino acid sequence of the protein. The sensitive positions are a proper subset of the positions in the amino acid sequence that significantly affect a prediction output generated by a prediction model by processing the amino acid sequence. For convenience, the process 1100 will be described as being performed by a system of one or more computers located in one or more locations. For example, a sensitivity analysis system, e.g., the sensitivity analysis system 500 of FIG. 5, appropriately programmed in accordance with this specification, can perform the process 1100.

The system obtains: (i) a prediction model that is configured to process data defining a sequence of amino acids to generate a prediction output that characterizes the sequence of amino acids, and (ii) data defining a particular sequence of amino acids corresponding to a particular protein (1102).

The system processes the data defining the particular sequence of amino acids using the prediction model to generate a particular prediction output (1104).

The system identifies one or more sensitive positions in the particular sequence of amino acids based on a sensitivity of the particular prediction output to the amino acids in the sensitive positions in the particular sequence of amino acids (1106).

The system presents a 3-D representation of the particular protein that depicts a folding structure of the particular protein (1108). The 3-D representation visually distinguishes the sensitive positions in the particular sequence of amino acids corresponding to the particular protein from positions in the particular sequence of amino acids corresponding to the particular protein that are not sensitive positions.

Figure 12:
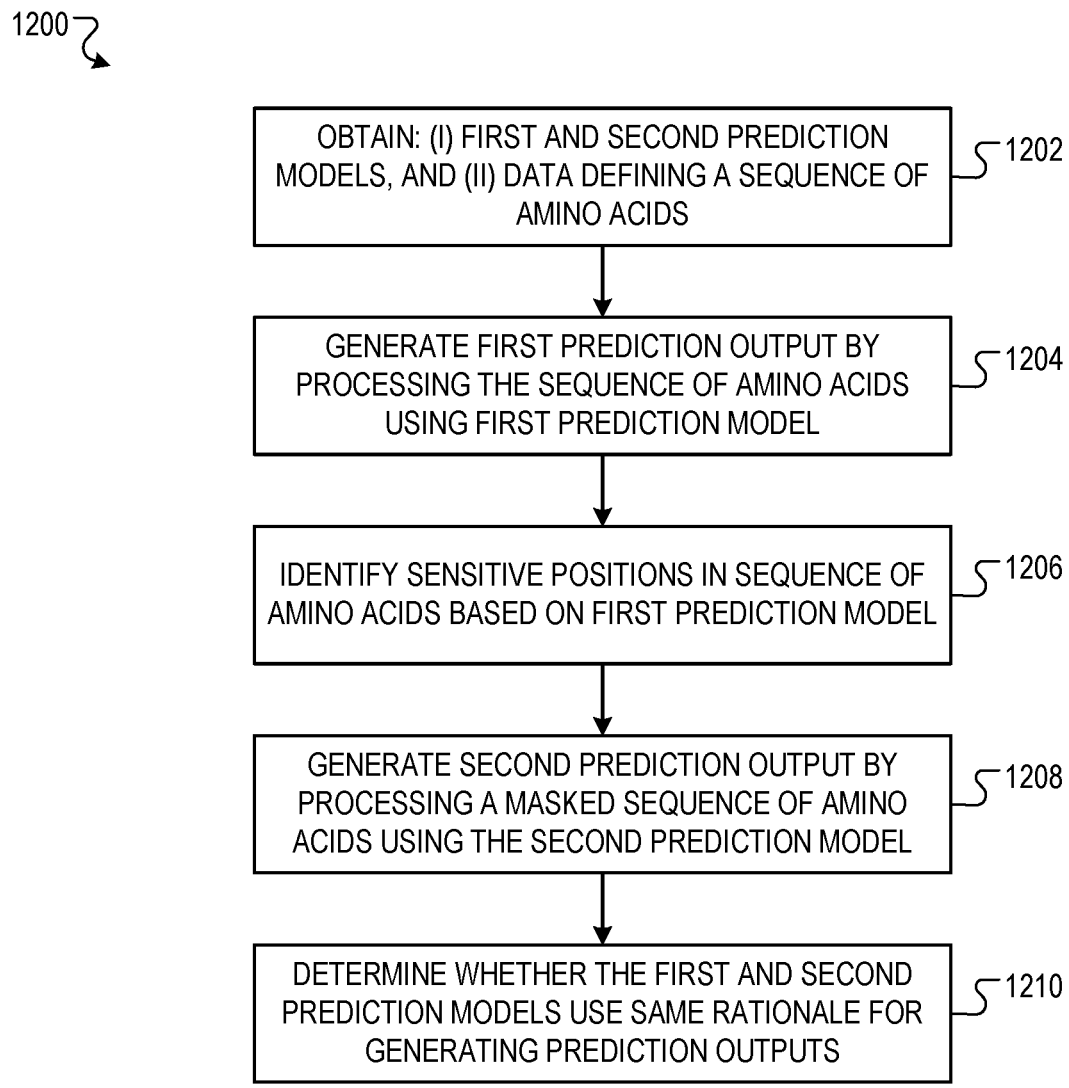
FIG. 12 is a flow diagram of an example process for determining whether a first prediction model and a second prediction model use a same rationale for generating prediction outputs.

FIG. 12 is a flow diagram of an example process 1200 for determining whether a first prediction model and a second prediction model use a same rationale for generating prediction outputs. For convenience, the process 1200 will be described as being performed by a system of one or more computers located in one or more locations. For example, a sensitivity analysis system, e.g., the sensitivity analysis system 500 of FIG. 5, appropriately programmed in accordance with this specification, can perform the process 1200.

The system obtains: (i) a first prediction model and a second prediction model that are both configured to process data defining a sequence of amino acids to generate a prediction output that characterizes the sequence of amino acids, and (ii) data defining a particular sequence of amino acids (1202).

The system processes the data defining the particular sequence of amino acids using the first prediction model to generate a first prediction output (1204).

The system identifies one or more sensitive positions in the particular sequence of amino acids based on a sensitivity of the first prediction output generated by the first prediction model to the amino acids in the sensitive positions in the particular sequence of amino acids (1206).

The system processes data defining a masked sequence of amino acids using the second prediction model to generate a second prediction output (1208). The masked sequence of amino acids matches the particular sequence of amino acids at each of the sensitive positions, and the masked sequence of amino acids includes a masked amino acid at each position that is not a sensitive position.

The system determines whether the first prediction model and the second prediction model use the same rationale for generating prediction outputs based on a similarity measure between the first prediction output and the second prediction output (1210).

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A method performed by one or more data processing apparatus, the method comprising:
    obtaining data defining a plurality of training amino acid sequences that each correspond to a respective protein;
    generating a respective embedding of each of the plurality of training amino acid sequences, comprising, for each training amino acid sequence:
        processing the data defining the training amino acid sequence using a neural network that is trained to generate an output that characterizes a predicted biological function of the training amino acid sequence; and
        identifying the embedding of the training amino acid sequence as an intermediate output generated by the neural network by processing the data defining the training amino acid sequence; and
    using the embeddings of the plurality of training amino acid sequences to identify a predicted biological function of a new protein.

2. The method of claim 1, wherein using the embeddings of the plurality of training amino acid sequences to identify the predicted biological function of the new protein comprises:
    generating an embedding of a new amino acid sequence corresponding to the new protein, comprising:
        processing data defining the new amino acid sequence using the neural network; and
        identifying the embedding of the new amino acid sequence as an intermediate output generated by the neural network by processing the data defining the new amino acid sequence; and
    identifying the predicted biological function of the new protein using: (i) the embeddings of the plurality of training amino acid sequences, and (ii) the embedding of the new amino acid sequence.

3. The method of claim 2, wherein identifying the predicted biological function of the new protein using: (i) the embeddings of the plurality of training amino acid sequences, and (ii) the embedding of the new amino acid sequence, comprises:
    determining, for each of multiple training amino acid sequences, a similarity measure between the embedding of the training amino acid sequence and the embedding of the new amino acid sequence;
    identifying a particular training amino acid sequence from among the multiple training amino acid sequences based on the determined similarity measures; and
    identifying the predicted biological function of the new protein as a biological function of the protein corresponding to the particular training amino acid sequence.

4. The method of claim 2, wherein identifying the predicted biological function of the new protein using: (i) the embeddings of the plurality of training amino acid sequences, and (ii) the embedding of the new amino acid sequence, comprises:
    generating a respective embedding corresponding to each of a plurality of biological functions using the embeddings of the plurality of training amino acid sequences;
    determining, for each of the plurality of biological functions, a similarity measure between the embedding corresponding to the biological function and the embedding of the new amino acid sequence; and
    identifying the predicted biological function of the new protein as a particular biological function from among the plurality of biological functions based on the determined similarity measures.

5. The method of claim 4, wherein generating an embedding corresponding to a biological function comprises:
    identifying one or more training amino acid sequences that correspond to respective proteins having the biological function; and
    generating the embedding corresponding to the biological function using the embeddings of the identified training amino acid sequences that correspond to proteins having the biological function.

6. The method of claim 1, further comprising applying a whitening transformation to the embeddings of the training amino acid sequences and the embedding of the new amino acid sequence prior to identifying the predicted protein family of the new protein.

7. The method of claim 1, wherein the neural network is a convolutional neural network comprising one or more dilated convolutional layers.

8. The method of claim 7, wherein for each training amino acid sequence, processing the data defining the training amino acid sequence using the neural network comprises:
    generating a respective representation of each amino acid in the training amino acid sequence using the one or more dilated convolutional layers;
    generate the embedding of the training amino acid sequence using the respective representation of each amino acid in the training amino acid sequence.

9. The method of claim 8, wherein generating the embedding of the training amino acid sequence using the respective representation of each amino acid in the training amino acid sequence comprises:
pooling the respective representation of each amino acid in the training amino acid sequence.

10. The method of claim 9, wherein pooling the respective representation of each amino acid in the training amino acid sequence comprises:
max-pooling the respective representation of each amino acid in the training amino acid sequence.

11. A system comprising:
one or more computers; and
one or more storage devices communicatively coupled to the one or more computers, wherein the one or more storage devices store instructions that, when executed by the one or more computers, cause the one or more computers to perform operations comprising:
obtaining data defining a plurality of training amino acid sequences that each correspond to a respective protein;
generating a respective embedding of each of the plurality of training amino acid sequences, comprising, for each training amino acid sequence:
processing the data defining the training amino acid sequence using a neural network that is trained to generate an output that characterizes a predicted biological function of the training amino acid sequence; and
identifying the embedding of the training amino acid sequence as an intermediate output generated by the neural network by processing the data defining the training amino acid sequence; and
using the embeddings of the plurality of training amino acid sequences to identify a predicted biological function of a new protein.

12. The system of claim 11, wherein using the embeddings of the plurality of training amino acid sequences to identify the predicted biological function of the new protein comprises:
generating an embedding of a new amino acid sequence corresponding to the new protein, comprising:
processing data defining the new amino acid sequence using the neural network; and
identifying the embedding of the new amino acid sequence as an intermediate output generated by the neural network by processing the data defining the new amino acid sequence; and
identifying the predicted biological function of the new protein using: (i) the embeddings of the plurality of training amino acid sequences, and (ii) the embedding of the new amino acid sequence.

13. The system of claim 12, wherein identifying the predicted biological function of the new protein using: (i) the embeddings of the plurality of training amino acid sequences, and (ii) the embedding of the new amino acid sequence, comprises:
determining, for each of multiple training amino acid sequences, a similarity measure between the embedding of the training amino acid sequence and the embedding of the new amino acid sequence;
identifying a particular training amino acid sequence from among the multiple training amino acid sequences based on the determined similarity measures; and
identifying the predicted biological function of the new protein as a biological function of the protein corresponding to the particular training amino acid sequence.

14. The system of claim 12, wherein identifying the predicted biological function of the new protein using: (i) the embeddings of the plurality of training amino acid sequences, and (ii) the embedding of the new amino acid sequence, comprises:
generating a respective embedding corresponding to each of a plurality of biological functions using the embeddings of the plurality of training amino acid sequences;
determining, for each of the plurality of biological functions, a similarity measure between the embedding corresponding to the biological function and the embedding of the new amino acid sequence; and
identifying the predicted biological function of the new protein as a particular biological function from among the plurality of biological functions based on the determined similarity measures.

15. The system of claim 14, wherein generating an embedding corresponding to a biological function comprises:
identifying one or more training amino acid sequences that correspond to respective proteins having the biological function; and
generating the embedding corresponding to the biological function using the embeddings of the identified training amino acid sequences that correspond to proteins having the biological function.

16. One or more non-transitory computer storage media storing instructions that when executed by one or more computers cause the one or more computers to perform operations comprising:
obtaining data defining a plurality of training amino acid sequences that each correspond to a respective protein;
generating a respective embedding of each of the plurality of training amino acid sequences, comprising, for each training amino acid sequence:
processing the data defining the training amino acid sequence using a neural network that is trained to generate an output that characterizes a predicted biological function of the training amino acid sequence; and
identifying the embedding of the training amino acid sequence as an intermediate output generated by the neural network by processing the data defining the training amino acid sequence; and
using the embeddings of the plurality of training amino acid sequences to identify a predicted biological function of a new protein.

17. The non-transitory computer storage media of claim 16, wherein using the embeddings of the plurality of training amino acid sequences to identify the predicted biological function of the new protein comprises:
generating an embedding of a new amino acid sequence corresponding to the new protein, comprising:
processing data defining the new amino acid sequence using the neural network; and
identifying the embedding of the new amino acid sequence as an intermediate output generated by the neural network by processing the data defining the new amino acid sequence; and
identifying the predicted biological function of the new protein using: (i) the embeddings of the plurality of training amino acid sequences, and (ii) the embedding of the new amino acid sequence.

18. The non-transitory computer storage media of claim 17, wherein identifying the predicted biological function of the new protein using: (i) the embeddings of the plurality of training amino acid sequences, and (ii) the embedding of the new amino acid sequence, comprises:

determining, for each of multiple training amino acid sequences, a similarity measure between the embedding of the training amino acid sequence and the embedding of the new amino acid sequence;

identifying a particular training amino acid sequence from among the multiple training amino acid sequences based on the determined similarity measures; and identifying the predicted biological function of the new protein as a biological function of the protein corresponding to the particular training amino acid sequence.

19. The non-transitory computer storage media of claim 17, wherein identifying the predicted biological function of the new protein using: (i) the embeddings of the plurality of training amino acid sequences, and (ii) the embedding of the new amino acid sequence, comprises:

generating a respective embedding corresponding to each of a plurality of biological functions using the embeddings of the plurality of training amino acid sequences;

determining, for each of the plurality of biological functions, a similarity measure between the embedding corresponding to the biological function and the embedding of the new amino acid sequence; and identifying the predicted biological function of the new protein as a particular biological function from among the plurality of biological functions based on the determined similarity measures.

20. The non-transitory computer storage media of claim 19, wherein generating an embedding corresponding to a biological function comprises:

identifying one or more training amino acid sequences that correspond to respective proteins having the biological function; and generating the embedding corresponding to the biological function using the embeddings of the identified training amino acid sequences that correspond to proteins having the biological function.

* * * * *